US008877976B2

(12) United States Patent
Lettmann et al.

(10) Patent No.: US 8,877,976 B2
(45) Date of Patent: Nov. 4, 2014

(54) PROCESS FOR PREPARING 3-AMINOMETHYL-3,5,5-TRIMETHYL-CYCLOHEXYLAMINE

(75) Inventors: Christian Lettmann, Coesfeld (DE); Guido Streukens, Wuppertal (DE); Matthias Orschel, Muenster (DE); Gerda Grund, Coesfeld (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/885,532

(22) PCT Filed: Nov. 17, 2011

(86) PCT No.: PCT/EP2011/070389
§ 371 (c)(1),
(2), (4) Date: May 15, 2013

(87) PCT Pub. No.: WO2012/076315
PCT Pub. Date: Jun. 14, 2012

(65) Prior Publication Data
US 2013/0261341 A1 Oct. 3, 2013

(30) Foreign Application Priority Data
Dec. 8, 2010 (DE) .......................... 10 2010 062 594

(51) Int. Cl.
*C07C 209/00* (2006.01)
*C07C 209/48* (2006.01)
*C07C 209/52* (2006.01)

(52) U.S. Cl.
CPC ............. *C07C 209/52* (2013.01); *C07C 209/48* (2013.01); *C07C 2101/14* (2013.01)
USPC ........... 564/448; 564/445; 564/446; 564/453; 564/461

(58) Field of Classification Search
None
See application file for complete search history.

(56) References Cited

U.S. PATENT DOCUMENTS

| 8,536,370 B2 | 9/2013 | Grund et al. |
| 2002/0137970 A1 | 9/2002 | Ostgard et al. |
| 2009/0048466 A1 | 2/2009 | Lettmann et al. |
| 2010/0041921 A1 | 2/2010 | Lettmann et al. |

FOREIGN PATENT DOCUMENTS

| EP | 0 394 967 | 10/1990 |
| EP | 1 216 985 | 6/2002 |
| WO | 2007 093240 | 8/2007 |
| WO | 2008 107226 | 9/2008 |
| WO | 2012 076317 | 6/2012 |

OTHER PUBLICATIONS

International Search Report Issued Apr. 24, 2012 in PCT/EP11/70389 Filed Nov. 17, 2011.
U.S. Appl. No. 13/991,718, filed Jun. 5, 2013, Galle, et al.
U.S. Appl. No. 13/990,602, filed May 30, 2013, Orschel, et al.
U.S. Appl. No. 14/116,233, filed Nov. 7, 2013, Orschel, et al.
U.S. Appl. No. 14/124,449, filed Dec. 6, 2013, Schwarz, et al.

*Primary Examiner* — Sudhakar Katakam
(74) *Attorney, Agent, or Firm* — Oblon, Spivak, McClelland, Maier & Neustadt, L.L.P.

(57) ABSTRACT

The invention relates to an improved process for preparing 3-aminomethyl-3,5,5-trimethylcyclohexylamine, referred to hereinafter as isophoronediamine or IPDA for short, by means of catalytic hydrogenation and/or catalytic reductive amination (also referred to as aminating hydrogenation) of 3-cyano-3,5,5-trimethylcyclohexanone, also called isophoronenitrile or IPN for short hereinafter.

24 Claims, No Drawings

PROCESS FOR PREPARING 3-AMINOMETHYL-3,5,5-TRIMETHYL-CYCLOHEXYLAMINE

CROSS REFERENCE TO RELATED APPLICATIONS

The present application is a 35 U.S.C. § 371 national stage patent application of International patent application PCT/EP11/70389, filed on Nov. 17, 2011, the text of which is incorporated by reference, and claims the benefit of the filing date of German Application No. 10 2010 062 594.9 filed on Dec. 8, 2010, the text of which is also incorporated by reference.

The invention relates to an improved process for preparing 3-aminomethyl-3,5,5-trimethylcyclohexylamine, referred to hereinafter as isophoronediamine or IPDA for short, by means of catalytic hydrogenation and/or catalytic reductive amination (also referred to as aminating hydrogenation) of 3-cyano-3,5,5-trimethylcyclohexanone, referred to hereinafter as isophoronenitrile or IPN for short.

The preparation of IPDA by aminating hydrogenation of IPN is known and has already been described many times.

In the simplest case (U.S. Pat. No. 3,352,913), IPN is reacted in the presence of hydrogen and of an excess of ammonia over a cobalt catalyst. First of all, IPN and ammonia form, through elimination of water, isophoronenitrileimine, IPNI, which is subsequently hydrogenated to IPDA.

Particular reference is made to the problem of elimination of HCN from gamma-ketonitriles, such as IPN, in the literature (U.S. Pat. No. 3,352,913). Firstly, it is noted that HCN elimination reduces the yield of IPDA (EP 042 119, DE 44 26 472).

Secondly, it is pointed out that HCN acts as a catalyst poison and leads to deactivation of the hydrogenation catalyst (EP 394 967 A1, page 2 line 34 ff, page 3 line 44 ff). It is therefore recommended that the imination step be performed in such a way that a minimum amount of HCN is eliminated. The process is preferably to be run such that less than 0.001 mol of HCN is eliminated per mole of nitrile used (EP 394 967 page 5 line 49 ff). Based on the aminating hydrogenation of IPN, this is 163 ppmw (0.0163 percent by weight).

As well as the reduction in the cyanide concentration, there are descriptions of further methods of increasing the yield of IPDA in the aminating hydrogenation of IPN IPDA.

As already mentioned above, an excess of ammonia or the use of ammonia as a solvent has a positive effect on the yield (e.g. EP 449 089, EP 659 734, DE 12 29 078).

Modification with alkali metal hydroxides (EP 729 937) also leads to an increase in the IPDA yield. The fact that the addition of alkali metal hydroxides, particularly lithium hydroxide, in nitrile hydrogenations can increase the yield of primary amine is known from several publications (U.S. Pat. No. 4,375,003, EP 913 388). The catalysts can either be treated with alkali metal hydroxides before the reaction, or

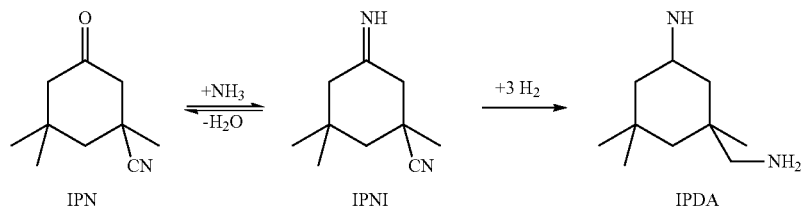

When the reaction is conducted in this way, the yield of IPDA is determined to a crucial degree by the excess of ammonia. The maximum IPDA yields achieved are about 80%. The main by-product is what is called the amino alcohol, IPAA, which results from the direct hydrogenation of the IPN.

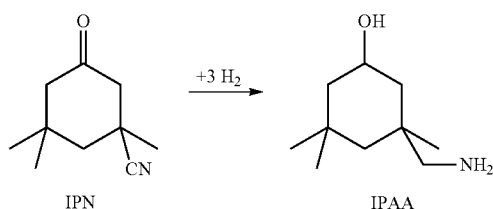

A significant rise in the IPDA yield is achieved when the formation of IPNI is accelerated by use of suitable imination catalysts. Suitable imination catalysts are, for example, acidic ion exchange resins (EP 042 119). In addition, it is also possible to use acidic metal oxides (EP 449 089), sulfo-containing organopolysiloxanes (EP 816 323), heteropolyacids (DE 44 26 472) and activated carbon (EP 061 137) as imination catalysts. As well as the reduction of the unwanted amino alcohol, other by-products are also distinctly suppressed, for example bicyclic compounds and those by-products which result from the elimination of HCN.

else the alkali metal hydroxide is added to the reaction mixture during the reaction. Unless any great amounts of solvents such as ammonia, THF or methanol are used, the long-term stability of the LiOH-modified catalysts is quite good. In in-house experiments, however, we have found that, in the case of use of the abovementioned solvents, the LiOH is continuously washed off the catalyst, and thus the proportion of secondary amines rises again. In the case of a continuous process regime in which the solvent is removed from the mixture by distillation and recycled into the process, there is additionally deposition of the alkali metal hydroxides in the distillation columns. The columns have to be shut down and cleaned at regular intervals, and so the alkali modification leads indirectly to production shutdowns.

According to EP 913 387, selectivity can also be enhanced in the preparation of IPDA by using quaternary ammonium bases. Correspondingly modified catalysts, specifically in the case of use of a solvent, have a much longer service life than alkali-modified catalysts.

The problem addressed by the present invention was that of finding a process for enhancing selectivity of the catalytic hydrogenation and/or the catalytic reductive amination of IPN to IPDA, which eliminates said disadvantages of the above-described processes.

It has now been found that, surprisingly, the problem can be solved by an increase in the cyanide ion concentration in the reaction mixture, for example caused by the controlled elimination of HCN from IPN. This is surprising in that cyanide ions have been described as catalyst poisons and therefore, according to the prior art, a minimum concentration of cyanide ions is desirable for yield optimization and selectivity optimization.

The increase in the cyanide ion concentration within a particular range surprisingly ensures a rise in selectivity for the same conversion in the hydrogenation of IPNI to IPDA.

The invention provides a process for preparing isophoronediamine by means of catalytic hydrogenation and/or catalytic reductive amination of isophoronenitrile (IPN), in the presence of ammonia, hydrogen and at least one catalyst and optionally a solvent or solvent mixture, where the cyanide ion concentration in the reaction mixture which is sent to the hydrogenation is 200 ppmw to 5000 ppmw, based on the isophoronenitrile used.

The setting of the cyanide ion concentration of 200 ppmw to 5000 ppmw, preferably to 3000, can be achieved by various measures, for example by controlled metered addition of HCN or cyanide salts such as KCN, or else by the use of suitable IPN qualities. In the process according to the invention, the setting of the cyanide ion concentration is preferably achieved by causing controlled redissociation of the IPN in the imination stage. Contrary to the teaching of EP 394 967 A1, this can in accordance with the invention by an increase in the temperature in the imination stage by 5-50 K, preferably 7-30 K, more preferably 10-20 K, above the temperature which, depending on the use of an imination catalyst, is needed to achieve a conversion of IPN to IPNI of at least 80% in the imination stage.

It is possible to perform the process according to the invention in one stage or in a plurality of stages.

If the process is performed in one stage, isophoronenitrile is subjected to aminating hydrogenation directly in the presence of ammonia, hydrogen, a hydrogenation catalyst and possibly further additions, and in the presence or absence of organic solvents.

The expression "in a plurality of stages" means that isophoronenitrile is first converted fully or partly in a separate reactor or reactor section to isophoronenitrileimine, and this isophoronenitrileimine is subjected to aminating hydrogenation as a pure substance or in a mixture with other components, in the presence of at least ammonia.

A preferred embodiment of the process according to the invention for preparing IPDA is a two-stage process: In the first stage, at least some of the IPN used, in the presence or absence of an imination catalyst and/or of solvents, is converted by reaction with ammonia to isophoronenitrileimine. The conversion of IPN to IPNI after the imination should be greater than 80%, preferably greater than 90%, more preferably greater than 95%. In the second stage, the first stage reaction product, as obtained or after a further treatment and/or addition of further ammonia, is subjected to aminating hydrogenation over hydrogenation catalysts in the presence of at least ammonia and hydrogen and in the presence or absence of an organic solvent at a temperature of 20 to 150° C., preferably 40 to 130° C., and a pressure of 0.3 to 50 MPa, preferably 5 to 30 MPa.

In a further preferred embodiment, the conversion of IPN to IPDA is effected in three separate reaction spaces. In the first reaction space, IPN is converted to isophoronenitrileimine with excess ammonia over imination catalysts at temperatures between 20 and 150° C. and pressures between 5 and 30 MPa. In the second reaction space, the reaction products formed are hydrogenated with hydrogen in the presence of excess ammonia over hydrogenation catalysts at temperatures between 20 and 130° C. and pressures of 5 to 30 MPa. In the third reaction space, the reaction products formed are hydrogenated over the catalysts for use in accordance with the invention at temperatures between 100 and 160° C. and pressures of 5 to 30 MPa.

In order to accelerate the establishment of equilibrium in the imination reaction, it is appropriate to use an imination catalyst. For this purpose, the imination catalysts known according to the prior art can be used. Suitable catalysts are, for example, inorganic or organic ion exchangers (see EP 042 119), supported heteropolyacids (see DE 44 26 472), acidic metal oxides, especially aluminum oxide and titanium dioxide (see EP 449 089), organopolysiloxanes containing sulfo groups (DE 196 27 265.3), and acidic zeolites and activated carbon (EP 061 137). In the case of use of an imination catalyst, the reaction temperature may be between 10 and 150° C., preferably between 30 and 130° C. and most preferably between 40 and 100° C. The pressure is between the autogenous pressure of the mixture and 50 MPa. Preference is given to performing the imination reaction at the pressure at which the subsequent reductive amination is also performed.

Even though the imination of isophoronenitrile with liquid ammonia is preferably performed without addition of further solvents, it is also possible to work in the presence of additional solvents. Suitable solvents are monohydric alcohols having 1 to 4 carbon atoms, especially methanol, and ethers, particularly THF, MTBE and dioxane.

In the imination stage, between 1 and 500 mol, preferably 5 and 200 mol, more preferably between 5 and 100 mol, of ammonia are used per mole of IPN used. Typical catalyst hourly space velocities are in the range from 0.01 to 10 kg of IPN per kg of catalyst and hour, preferably 0.5 to 10 and more preferably 0.5 to 5 kg of IPN per kg of catalyst and hour.

In the case of imination in the presence of an imination catalyst, the catalyst may be present in the form of a suspension catalyst or fixed bed catalyst. It is advantageous to use fixed bed catalysts. In a particularly preferred embodiment, IPN and ammonia are passed continuously from the bottom upward through a reaction tube filled with imination catalyst.

The hydrogenation is typically effected at temperatures between 20 and 150° C., preferably 40 and 130° C., and pressures of 0.3 to 50 MPa, preferably 5 to 30 MPa. It is also possible to perform the hydrogenation in the presence of the solvents already mentioned for the imination stage. The main advantage in the case of use of a solvent is that the hydrogenation can be performed at lower pressures between 0.3 and 10 MPa.

The hydrogen required for the hydrogenation can be supplied to the reactor either in excess, for example at up to 10 000 molar equivalents, or only in such an amount that the hydrogen consumed by reaction and the portion of the hydrogen which leaves the reactor dissolved in the product stream is replenished. In the case of a continuous mode of operation, the hydrogen can be supplied in cocurrent or countercurrent.

In a preferred embodiment, the hydrogenation is effected in liquid ammonia as solvent. Between 1 and 500 mol, preferably 5 and 200 mol, more preferably between 5 and 100 mol, of ammonia are used per mole of IPN. It is appropriate to use at least the amount of ammonia which has been established in the upstream imination. However, the ammonia content can also be increased to the desired value before the hydrogenation by addition of additional ammonia.

The catalysts used may in principle be any catalysts which catalyze the hydrogenation of nitrile and/or imine groups with hydrogen. Particularly suitable catalysts are nickel, copper, iron, palladium, rhodium, ruthenium and cobalt catalysts, very particularly ruthenium and cobalt catalysts. To increase the activity, selectivity and/or service life, the catalysts may additionally comprise doping metals or other modifiers. Typical doping metals are, for example, Mo, Fe, Ag, Cr, Ni, V, Ga, In, Bi, Ti, Zr and Mn, and the rare earths. Typical modifiers are, for example, those with which the acid-base properties of the catalysts can be influenced, preferably alkali metals and alkaline earth metals or compounds thereof, preferably magnesium and calcium compounds, and also phosphoric acid or sulfuric acid and compounds thereof.

The catalysts can be used in the form of powders or shaped bodies, for example extrudates or compressed powders. It is possible to employ unsupported catalysts, Raney-type catalysts or supported catalysts. Preference is given to Raney-type and supported catalysts. Suitable support materials are, for example, silicon dioxide, aluminum oxide, aluminosilicates, titanium dioxide, zirconium dioxide, kieselguhr, aluminum-silicon mixed oxides, magnesium oxide and activated carbon. The active metal can be applied to the support material in a manner known to those skilled in the art, for example by impregnation, spray application or precipitation. According to the method of catalyst production, further preparation steps known to those skilled in the art are necessary, for example drying, calcination, shaping and activation. For shaping, it is optionally possible to add further assistants, for example graphite or magnesium stearate. The required volume of the hydrogenation catalysts to be used is guided by the LHSV (liquid hourly space velocity), which is dependent on the operating pressure, the temperature, the concentration and the catalyst activity and has to be observed in order to ensure maximum completeness of hydrogenation of the IPN used. Typically, the LHSV in the case of use of the mixture of IPN, ammonia and hydrogen, the use of which is preferred, is between 0.5 and 4 liters of IPN/ammonia mixture per liter of catalyst and hour, preferably between 1 and 3 $I_{sol} I_{cat}^{-1} h^{-1}$.

It is preferable that the hydrogenation catalysts for use are first conditioned with ammonia before they are used in the hydrogenation. For this purpose, the catalysts are contacted with ammonia or with mixtures of ammonia and one or more solvents. The conditioning preferably follows installation of the catalysts in the hydrogenation reactor, but it can also precede the installation of the catalysts. For conditioning, between 0.2 and 3, preferably 0.5 and 2, m³ of ammonia per m³ of catalyst and hour are used. It is customary to work at temperatures between 20 and 150° C., preferably 40 to 130° C. Particular preference is given to running through a temperature ramp in which the catalyst, beginning at moderately elevated temperature, preferably between 20 and 50° C., is heated gradually up to the reaction temperature desired at a later stage for the hydrogenation, preferably 20 to 150° C. The conditioning is preferably performed in the presence of hydrogen, the partial pressure of the hydrogen used in the reactor covering the range from 0.1 to 50 MPa, preferably 5 to 40 MPa, more preferably 10 to 30 MPa. The duration of the conditioning, depending on the amount of ammonia used, is preferably between 1 and 48 h, more preferably between 12 and 24 h.

In the preferred two-stage process, the mixture comprising isophoronenitrileimine is hydrogenated with the aid of a shaped hydrogenation catalyst in the second stage. The mixture supplied to the hydrogenation stage may directly be any which is obtained in the imination of IPN with ammonia in the first stage, or as obtained after addition or removal of components, for example ammonia, organic solvents, bases, cocatalysts, cyanide salts, hydrocyanic acid and/or water. Preference is given to performing the hydrogenation continuously in fixed bed reactors which can be operated in trickle mode or liquid phase mode. Suitable reactor types are, for example, shaft furnaces, tray reactors or shell and tube reactors. It is also possible to connect a plurality of fixed bed reactors in series for the hydrogenation, in which case each of the reactors is operated either in trickle bed mode or liquid phase mode.

Apart from the aforementioned constituents of the mixture to be supplied to the imination stage, this may additionally comprise higher- or lower-boiling fractions than IPDA from the distillative workup of the reaction mixture drawn off from the trickle bed reactor. Such fractions may, apart from residues of IPDA, also comprise those by-products from which IPDA forms again under reaction conditions. It is particularly advantageous to recycle the higher-boiling fraction than IPDA, which, apart from residues of IPDA, comprises 2-aza-4,6,6-trimethylbicyclo[3.2.1]octane as the main product. It is likewise particularly advantageous to recycle incompletely converted IPN, especially fractions comprising isophoroneaminonitrile. The recycled material can also, if desired, be added directly to the reaction mixture to be supplied to the hydrogenation stage.

In the hydrogenation of IPN or isophoronenitrileimine, it is possible to form two different stereoisomers. Through the choice of a temperature profile in the hydrogenation step, it is possible to influence the isomer ratio. It is possible, for example, first to partly hydrogenate a mixture comprising IPN or isophoronenitrileimine at a temperature between 20 and 90° C., and then to complete the reaction in a second step within a temperature range between 90 and 150° C. The observation of relatively low reaction temperatures in the 1st step can shift the selectivity in favor of the cis isomer. The observation of relatively low reaction temperatures at the start of the reaction additionally has the advantage that the thermally labile isophoronenitrileimine is hydrogenated under particularly gentle conditions, and side reactions are suppressed as a result. Isophoroneaminonitrile, which is formed as an intermediate, is much more thermally stable and can therefore be hydrogenated at higher temperatures without any risk of further side reactions. The unwanted side reactions also include the elimination of HCN. In the process according to the invention, a certain cyanide ion concentration has a positive effect on the selectivity of the hydrogenation stage. This effect becomes increasingly apparent when the cyanide ions are present from the start in the hydrogenation stage and not just formed during the hydrogenation. Therefore, elimination of HCN during the hydrogenation stage should be avoided.

The desired temperature profile can be implemented, for example, by the series connection of two or more separately heatable reactors. It is also possible to implement a rising temperature profile in only one hydrogenation reactor. Particular preference is given to performing the hydrogenation reaction in an adiabatic trickle bed reactor, in which the reaction mixture is supplied to the reactor at temperatures between 20 and 90° C., and owing to the heat of reaction which occurs and is absorbed by the reaction mixture leaves it again between 90 and 150° C.

The reaction mixture leaving the hydrogenation is purified further by the customary methods, in order to obtain an IPDA with the desired quality. It is possible here to use all standard separation methods, for example distillation, flash evaporation, crystallization, extraction, sorption, permeation, phase separation or combinations of the above. The purification can be performed continuously, batchwise, in one or more stages, under reduced pressure or under pressure. Possible components which are removed, for example, in the further purification are hydrogen, ammonia, water, and by-products obtained in the preparation of IPDA from IPN, for example hydrogenated HCN elimination products or impurities in the IPN, methylated by-products and/or incompletely hydrogenated intermediates.

Preferably, the purification is achieved by distillation under pressure and/or under reduced pressure in a plurality of steps. For this purpose, it is possible to use any desired distillation columns with or without internals, for example dephlegmators, dividing walls, unordered internals or random packings, ordered internals or structured packings, or trays with or without forced flow.

In a first step, especially hydrogen, inert gases, ammonia, low-boiling impurities and possibly also water are removed fully or partly in one or more distillation columns. The removal is preferably effected at a pressure lower than in the reaction step. If the removal is effected in a plurality of distillation steps, it is advantageous to lower the pressure stepwise. Most preferably, the removal is effected above 1 bar and with bottom temperatures of 0-200° C. The use of a stripping gas for removal of low-boiling impurities may be advantageous. Especially ammonia and hydrogen and proportions of the low-boiling impurities can be recycled fully or partly into the process (reaction). The low-boiling impurities and possibly proportions of hydrogen and ammonia are sent to thermal utilization.

In a second step, low-boiling impurities, water and high-boiling impurities are fully or partly removed. This can be effected in one or more distillation columns. This may involve distilling water off together with organic, low-boiling impurities and possibly proportions of IPDA via the top of the column and, after condensation, separating them into an aqueous phase and an organic phase. In this case, the organic phase can be recycled partly as reflux into the column. If the second step of the distillation is performed in a single column (for example a dividing wall column), the IPDA is withdrawn via a sidestream with the desired purity, while the high-boiling impurities are obtained in the bottom of the column. If the separation, however, is performed in two or more stages, the IPDA is obtained at the top of a column. The low- and high-boiling impurities and water are preferably removed under a reduced pressure between 100 Pa and 0.0999 MPa and bottom temperatures of 50-300° C. All secondary components can be sent to thermal utilization.

The present invention is thus particularly characterized in that, contrary to the prior art to date, the selectivity of the reductive amination of IPN to IPDA is not maximized through the explicit minimization of the cyanide ion concentration. Instead, a minimum concentration of 200 ppmw based on the mass of IPN used is beneficial for the selectivity of the hydrogenation of the IPNI to IPDA. More particularly, the formation of the bicyclic compound 2-aza-4,6,6-trimethylbicyclo[3.2.1]octane, a main by-product in the reductive amination of IPN to IPDA, which is formed by the intramolecular nucleophilic attack of the amine group of IPAN on the carbon atom of the nitrile group, is significantly reduced.

Examples 1 and 2 show two comparable experimental settings which differ solely by the cyanide ion concentration in the feed. It becomes clear that the metered addition of an amount of cyanide corresponding to 1000 ppmw of HCN reduces the amount of bicyclic amine formed from 4.13% to 2.03%. The amidine intermediate is lowered from 1.40% to 1.00%. Since no reduced activity was detected (conversion of IPN and IPAN constant), the yield of IPDA in the crude product rises from 93.23% to 95.69%. As well as the positive influence on the selectivity, however, the cyanide ions also have the parallel poisoning effect, described in the literature, on hydrogenation catalysts. Therefore, an excessive increase in the cyanide ion concentration is not productive, since the deactivating action otherwise becomes dominant. Preference is given to a concentration based on the IPN used of not more than 3000 ppmw. A distinctly higher cyanide concentration of in this case 5000 ppmw, based on the IPN used still ensures reduced by-product concentrations (bicyclic amine 2.36%, amidine 1.03%), but the proportion of unconverted IPAN rises from 0.63% to 1.15%, as a result of which the overall yield of IPDA at 94.62% falls by one percentage point. This is illustrated in Example 3.

EXAMPLES

In examples 1-3, the cyanide was added manually. This ensures comparable conditions among the results. However, preference is given in accordance with the invention to the production of the cyanide ions in the prereactor.

Description of the continuous experimental apparatus:

IPN and ammonia are mixed continuously in a vessel. From there, the mixture passes through a pump into the 2 l prereactor, which is filled with ion exchanger according to EP 042 119 for catalysis of imine formation from IPN and ammonia. Subsequently, the mixture is hydrogenated in a 6 l trickle bed reactor with three individually heatable temperature zones. After the reaction, the ammonia is removed and recycled into the process; in addition, consumed ammonia is replaced continuously.

Example 1

In the above-described experimental apparatus, a 21.5% ammoniacal IPN solution was subjected to aminating hydrogenation at an LHSV of 1.8 $I_{sol} I_{cat}^{-1} h^{-1}$. The catalyst used was a cobalt catalyst supported on kieselguhr. The pressure in the plant was 252 bar. The temperature profile established in the hydrogenation corresponds to an adiabatic reaction regime; the temperature at the reactor inlet was 70° C., and at the outlet 115° C. The mixture leaving the reaction section was analyzed by gas chromatography. The composition is shown in table 1.

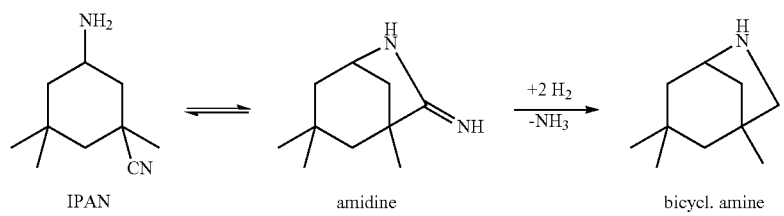

TABLE 1

| Substance | Proportion by GC |
|---|---|
| IPDA | 93.23 |
| IPN | 0.00 |
| IPAN | 0.71 |
| TMCA | 0.11 |
| bicycl. amine | 4.13 |
| amidine | 1.40 |
| Sum of other unknown by-products | 0.28 |
| Sum of unknowns | 0.14 |

Example 2

As example 1, except that 40 g/h of a 10% aqueous KCN solution were additionally metered in downstream of the imination reactor. This corresponds to a space velocity of 1000 ppmw of HCN based on IPN. The results of the gas chromatography analysis of the reaction product are shown in table 2:

TABLE 2

| Substance | Proportion by GC |
|---|---|
| IPDA | 95.69 |
| IPN | 0.00 |
| IPAN | 0.63 |
| TMCA | 0.09 |
| bicycl. amine | 2.03 |
| amidine | 1.00 |
| Sum of other unknown by-products | 0.42 |
| Sum of unknowns | 0.14 |

Example 3

As example 1, except that 100 g/h of a 20% aqueous KCN solution were additionally metered in downstream of the imination reactor. This corresponds to a space velocity of 5000 ppmw of HCN based on IPN. The results of the gas chromatography analysis of the reaction product are shown in table 3:

TABLE 3

| Substance | Proportion by GC |
|---|---|
| IPDA | 94.62 |
| IPN | 0.00 |
| IPAN | 1.15 |
| TMCA | 0.24 |
| bicycl. amine | 2.36 |
| amidine | 1.03 |
| Sum of other unknown by-products | 0.47 |
| Sum of unknowns | 0.13 |

The invention claimed is:

1. A process for preparing isophoronediamine, the process comprising:
    reacting isophoronenitrile with ammonia optionally in the presence of at least one of an imination catalyst and a solvent to obtain a first product comprising isophoronenitrileimine with a conversion of isophoronenitrile to isophoronenitrileimine of greater than 80%,
    subjecting a reaction mixture comprising the first product as obtained from said reacting or after a further treatment to aminating hydrogenation over a hydrogenation catalyst in the presence of ammonia, hydrogen, and optionally an organic solvent at a temperature of from 20 to 150° C. and a pressure of from 0.3 to 50 MPa, thereby obtaining a second product comprising isophoronediamine,
    wherein a cyanide ion concentration in the reaction mixture subjected to the aminating hydrogenation is of from 200 ppmw to 5000 ppmw, based on an amount of the isophoronenitrile added.

2. The process of claim 1,
wherein the cyanide ion concentration in the reaction mixture is of from 200 ppmw to 3000 ppmw.

3. The process of claim 1,
wherein the cyanide ion concentration is adjusted by controlled metered addition of HCN or a cyanide salt or with an isophoronenitrile quality having the cyanide ion concentration of from 200 ppmw to 5000 ppmw.

4. The process of claim 1,
wherein the cyanide ion concentration is adjusted by controlled redissociation of the isophoronenitrile in said reacting.

5. The process of claim 4,
wherein the cyanide ion concentration is adjusted by increasing a temperature in said reacting by 5-50 K above a temperature which, depending on the presence of the imination catalyst, is needed to achieve the conversion of isophoronenitrile to isophoronenitrileimine of at least 80%.

6. The process of claim 1,
wherein isophoronenitrile is converted to isophoronediamine in three separate reaction spaces:
    in a first reaction space, isophoronenitrile is converted to isophoronenitrileimine with excess ammonia over the imination catalyst at a temperature of from 20 to 150° C. and a pressure of from 5 to 30 MPa, thereby forming a first reaction product;
    in a second reaction space, the first reaction product is hydrogenated with hydrogen in the presence of excess ammonia over a first hydrogenation catalyst at a temperature of from 20 to 130° C. and a pressure of from 5 to 30 MPa, thereby forming a second reaction product; and
    in a third reaction space, the second reaction product is hydrogenated over a second hydrogenation catalyst at a temperature of from 100 to 160° C. and a pressure of from 5 to 30 MPa.

7. The process of claim 1,
wherein said reacting occurs in the presence of an imination catalyst.

8. The process of claim 1, wherein
liquid ammonia is used in said reacting, which occurs without additional solvent.

9. The process of claim 1,
wherein an amount of from 1 to 500 mol of ammonia is added per mole of the isophoronenitrile added in said reacting.

10. The process of claim 1,
wherein said reacting occurs in the presence of a suspension catalyst or a fixed bed catalyst.

11. The process of claim 1,
wherein isophoronenitrile and ammonia in said reacting are conducted continuously from a bottom upward through a reaction tube filled with the imination catalyst.

12. The process of claim 1,
wherein in said subjecting, hydrogen is supplied either in excess, or in such an amount that the hydrogen consumed in said subjecting and the hydrogen dissolved in the second product is replenished.

13. The process of claim 1,
wherein said subjecting is performed in liquid ammonia as a solvent, in an amount of from 1 to 500 mol of the ammonia per mole of isophoronenitrile.

14. The process of claim 1,
wherein the hydrogenation catalyst is nickel, copper, iron, palladium, rhodium, ruthenium, cobalt, or a combination thereof.

15. The process of claim 1, wherein the hydrogenation catalyst comprises a doping metal.

16. The process of claim 1, wherein the hydrogenation catalyst comprises a modifier.

17. The process of claim 1, wherein the hydrogenation catalyst is added in a form of a powder or a shaped body.

18. The process of claim 1,
wherein the hydrogenation catalyst is an unsupported catalyst, a Raney-type catalyst, or a supported catalyst.

19. The process of claim 18,
wherein a support material for the supported catalyst is selected from the group consisting of silicon dioxide, aluminum oxide, an aluminosilicate, titanium dioxide, zirconium dioxide, kieselguhr, an aluminum-silicon mixed oxide, magnesium oxide, and activated carbon.

20. The process of claim 1,
wherein the hydrogenation catalyst is conditioned with ammonia prior to said subjecting.

21. The process of claim 1,
wherein in said subjecting, the reaction mixture is hydrogenated in the presence of a shaped hydrogenation catalyst.

22. The process of claim 1,
wherein said subjecting is performed continuously in a fixed bed reactor operated in a trickle mode or a liquid phase mode.

23. The process of claim 1, further comprising:
purifying the second product in one or more stages, thereby obtaining isophoronediamine.

24. The process of claim 1, further comprising:
purifying the second product in two stages, thereby obtaining isophoronediamine,
wherein
in a first stage, hydrogen, inert gases, ammonia, low-boiling impurities, and optionally water are completely or partially removed in at least one distillation column, and
in a second stage, additional low-boiling impurities, water and high-boiling impurities are completely or partially removed in the at least one distillation column.

\* \* \* \* \*